(12) United States Patent
Jacquot et al.

(10) Patent No.: US 9,704,095 B2
(45) Date of Patent: Jul. 11, 2017

(54) METHOD FOR TRANSCRIBING AN ODOR OR AN AROMA INTO COLOR INFORMATION, AND METHOD FOR TRANSCRIBING COLOR INFORMATION INTO A LIST OF MOLECULES

(71) Applicant: UNIVERSITE DE LORRAINE, Nancy (FR)

(72) Inventors: Muriel Jacquot, Rosieres aux Salines (FR); Yelena Maric, Nancy (FR); Thierry Lambert, Villers-les-Nancy (FR)

(73) Assignee: UNIVERSITE DE LORRAINE, Nancy (FR)

( * ) Notice: Subject to any disclaimer, the term of this patent is extended or adjusted under 35 U.S.C. 154(b) by 406 days.

(21) Appl. No.: 14/409,193

(22) PCT Filed: Jun. 14, 2013

(86) PCT No.: PCT/EP2013/062388
§ 371 (c)(1),
(2) Date: Dec. 18, 2014

(87) PCT Pub. No.: WO2013/189852
PCT Pub. Date: Dec. 27, 2013

(65) Prior Publication Data
US 2015/0170026 A1 Jun. 18, 2015

(30) Foreign Application Priority Data
Jun. 18, 2012 (FR) .................................... 12 55688

(51) Int. Cl.
*G06N 3/08* (2006.01)
*G01N 33/00* (2006.01)
(Continued)

(52) U.S. Cl.
CPC .......... *G06N 3/08* (2013.01); *G01N 33/0034* (2013.01); *G06N 3/04* (2013.01); *G06Q 30/02* (2013.01)

(58) Field of Classification Search
None
See application file for complete search history.

(56) References Cited

U.S. PATENT DOCUMENTS

2008/0010146 A1 1/2008 Gillespie et al.

FOREIGN PATENT DOCUMENTS

EP 1566633 A1 8/2005

OTHER PUBLICATIONS

Huang et al., A novel technique for rapid evaluation of fish freshness using colorimetric sensor array, Apr. 3, 2011, Journal of Food Engineering, 105, pp. 632-637.*

(Continued)

*Primary Examiner* — Alan Chen
(74) *Attorney, Agent, or Firm* — Baker & Hostetler LLP

(57) ABSTRACT

A method for transcribing an odor or an aroma into a colorimetric description comprises: physico-chemical analysis of said odor or of said aroma in order to associate with it a physico-chemical description comprising a physico-chemical vector, comprising proportions associated with a predetermined set of respective volatile molecules; physico-chemical analysis of a set of so-called test odors and/or aromas in order to assign to each test odor or aroma of said set a so-called test physico-chemical description comprising a so-called test physico-chemical vector comprising test proportions associated with said predetermined set of respective volatile molecules; assigning to the test odors and/or aromas respective test colorimetric descriptions comprising so-called test proportions associated with a set of respective colors; assigning to the odor or to the aroma (Continued)

a colorimetric description comprising proportions associated with said respective colors.

17 Claims, 5 Drawing Sheets

(51) Int. Cl.
  *G06Q 30/02* (2012.01)
  *G06N 3/04* (2006.01)

(56) References Cited

OTHER PUBLICATIONS

Nakamoto, Colorimetric method for odor discrimination using dye-coated plate and multiLED sensor, 2006, Sensors and Actuators B, 116, pp. 202-206.*

M. Penza, et al., "Application of Principal Component Analysis and Artificial Neural Networks to Recognize the Individual VOCs of Methanol/2-Propanol in a Binary Mixture by SAW Multi-Sensor Array", Sensors and Actuators B: Chemical: International Journal Devoted to Research and Development of Physical and Chemical Transducers, Apr. 1, 2003, pp. 269-284, vol. 89, No. 3, Elsevier A.S., Switzerland, XP004414880.

Yu-Jin Kim, "Can Eyes Smell? Cross-Modal Correspondences Between Color Hue-Tone and Fragrance Family", Color Research & Application, Oct. 31, 2011, pp. 139-156, vol. 38, No. 2, XP 055055930.

Yelena Maric, et al., "Contribution to Understanding Odour-Colour Association", Food Quality and Preference, May 11, 2012, pp. 191-195, vol. 27, No. 2, XP055055931.

* cited by examiner

METHOD FOR TRANSCRIBING AN ODOR OR AN AROMA INTO COLOR INFORMATION, AND METHOD FOR TRANSCRIBING COLOR INFORMATION INTO A LIST OF MOLECULES

CROSS-REFERENCE TO RELATED APPLICATIONS

This application is a National Stage of International patent application PCT/EP2013/062388, filed on Jun. 14, 2013, which claims priority to foreign French patent application No. FR 1255688, filed on Jun. 18, 2012, the disclosures of which are incorporated by reference in their entirety.

FIELD OF THE INVENTION

The field of the invention is that of the objective identification of sets of volatile molecules that can correspond to an odor or to an aroma.

BACKGROUND

A real need has emerged, notably in the means that can be developed for retranscribing authenticity or traceability in the field of olfactory marks, of the development of packages, or even in the dietary field.

In effect, it can be particularly advantageous to link a color or a set of colors to an odor or to an aroma, the visual data being less complex and more easy to recognize. This type of correlation can be applicable in all fields of business in which there is a need to transcribe, objectively, an odorous mixture into a set of objective parameters, notably into objective colorimetric data and vice-versa.

Currently, this assignment is done in a human manner. Expert judges are asked to make a sensory evaluation to produce colored odor profiles, that is to say assign a color or a plurality of colors to an odor.

This solution is unsatisfactory because of the difficulty in training the judges and of the time-consuming and costly nature of this type of measurement. Furthermore, because of the hedonic valency of the odors, this type of recognition method entails many tests, and the panel of judges needs to be very large to limit the variability and obtain reliable results. This solution does not make it possible to accurately describe an odor by means of a set of colors or to assign a color, even a panel of colors, to a new odor which has not been previously tested by the judges. In other words, a colored profile cannot be assigned to a new odor without it being done by a panel of judges, which as has previously been stated, is time-consuming because of the need to train the judges and to involve a panel of judges which is large enough to obtain a chromatic profile which is as objective as possible. Finally, it is not possible, via this method, to perform the reverse step which is to assign an odor or an aroma to a panel of colors.

The problem that the invention sets out to resolve is to propose a method that makes it possible to objectively assign a chromatic profile to any odorous mixture (and vice-versa) that makes it possible to obviate all or some of the drawbacks listed previously.

SUMMARY OF THE INVENTION

To this end, the subject of the invention is a method for transcribing an odor or an aroma into a colorimetric description comprising the following steps:

a first step of physico-chemical analysis of said odor or of said aroma in order to associate with it a physico-chemical description comprising a physico-chemical vector, comprising proportions associated with a predetermined set of respective volatile molecules, a second step of physico-chemical analysis of a set of so-called test odors and/or aromas in order to assign to each test odor or aroma of said set a so-called test physico-chemical description comprising a so-called test physico-chemical vector comprising test proportions associated with said predetermined set of respective volatile molecules, a step of assigning to the test odors and/or aromas respective test colorimetric descriptions comprising so-called test proportions associated with a set of respective colors, a step of assigning to the odor or to the aroma a colorimetric description comprising proportions associated with said respective colors, said assignment step comprising a first step of assigning to the odor or to the aroma a theoretical colorimetric description comprising theoretical colorimetric proportions associated with said respective colors, this first assignment step being performed by means of a first artificial neural network exhibiting a layered architecture, by presenting to it, as input, the physico-chemical vector, said first neural network generating, as output, said theoretical colorimetric description, said first neural network being previously subjected to a first learning step during which there are supplied to it, as input, physico-chemical vectors associated with the set of test odors and/or aromas, said first learning step being performed in a supervised manner by taking into account the test colorimetric descriptions associated with the set of respective test odors and/or aromas.

Advantageously, the method comprises, prior to the first learning step, a fixing step during which weights of first synaptic links linking neurons of said neural network two by two are set such that the weights associated with the first synaptic links are not modifiable during the learning step.

Advantageously, the fixing step is performed from first correlation coefficients, each first correlation coefficient being computed between a molecule of the set of molecules and a color of the set of colors, computed in a preliminary step from test physico-chemical vectors and colorimetric descriptions associated with the test odors and/or aromas (to which said physico-chemical vectors are assigned).

Advantageously, the preliminary step comprises, for at least one color of index j:

a step of selecting, from the set of test odors and/or aromas, a subset of index j of test odors and/or aromas which are associated with test colorimetric descriptions exhibiting non-zero proportions for said color of index j, a first step of grouping together test odors and/or aromas of the subset of index j in a set of groups of test odors and/or aromas, such that the physico-chemical vectors associated with the test odors and/or aromas present in a group exhibit, between one another, greater first correlation coefficients than with the physico-chemical vectors associated with the test odors and/or aromas present in the other groups of said set of groups, and, for at least one of said groups, a step of preparing a list of common molecules corresponding to the molecules for which the test proportion is non-zero in all the test physico-chemical vectors associated with the test odors and/or aromas grouped together in said group, and, for at least one molecule taken from the list of common molecules, a step during which a first series is established, in which the test odors and/or aromas grouped together in said group are arranged in ascending order of the proportion of said molecule in the test physico-chemical vectors associated with said test odors and/or aromas, a step during which a second series is established, in which the test odors and/or aromas grouped together in said group are arranged in ascending order of the proportion of said color in the colorimetric descriptions associated with said test odors and/or aromas, a step of computing another correlation coefficient between the first series and the second series, a step of computing at least one first correlation coefficient between a molecule of the set of molecules and a color of the set of colors from the other correlation coefficients computed for said molecule and said color.

This feature makes it possible to facilitate the learning of the neural network.

According to one embodiment, the colorimetric description is the theoretical colorimetric description.

According to another embodiment, the step of assigning the colorimetric description comprises a step of enhancing the theoretical colorimetric description from values of a set of sensory descriptors assigned to the odor or to the aroma and to respective test odors and/or aromas so as to obtain said colorimetric description, the set of sensory descriptors comprising at least one sensory descriptor taken from a source of an odor or of an aroma, a wholesomeness index, an agreeability index, a familiarity index, an olfactory note, and an intensity index.

This feature makes it possible to refine the theoretic chromatic profile (colorimetric description) by incorporating the hedonic valence of the odor or of the aroma.

Advantageously, the enhancement step comprises:

a step of submitting at least one second artificial neural network of index b to a second learning step, a second neural network exhibiting a layered architecture comprising an input layer suitable for receiving values associated with the set of sensory descriptors and supplying as output first Lm, second cm and third Hpm mean coordinates, in which p is an integer ranging from 1 to v an integer, in a colorimetric reference frame called L, C, H, said second neural network receiving, during the second learning step, values of the set of sensory descriptors associated with the test odors and/or aromas present in a color series made up of at least a part of the test odors and/or aromas of the set of test odors and/or aromas, a second step of analysis (of the odor or of the aroma) by supplying the values of the set of sensory descriptors as input for said second neural network of index b which supplies, as output, first Lmbutb, second cmbutb and third Hpmbutb target mean coordinates of index b in the reference frame L, H, C of a target colorimetric description associated with the odor or with the aroma concerned, a step of computing a new colorimetric description comprising new proportions $qcnb_j$ which observe, regardless of the value of j between 1 and J, the following equations:

$$Lmbutb = \sum_{j=1}^{J} Lj * qcnb_j$$

$$cmbutb = \sum_{j=1}^{J} cj * qcnb_j,$$

$$Hpmbutb = \sum_{j=1}^{J} PHpj * qcnb_j$$

with p an integer ranging from 1 to v and v an integer, in which Lj, cj and PHpj are the respective coordinates of the color Cj of index j in the reference frame L, H, C, and which minimize, for at least one color Cj, the absolute value $|qcnb_j - qcTb_j|$ of the difference between the new proportion of order b and the theoretical proportion of order b.

Advantageously, the method comprises, prior to the enhancement step, a second step of grouping together test odors and/or aromas belonging to the set of test odors and/or aromas in a set of series, called color series, by similarity of test colorimetric descriptions which are assigned to them.

Advantageously, the method comprises:

a step of computing coefficients similarity of between the odor and the respective color series, from values of the set of sensory descriptors assigned to the odor or to the aroma and to the test odors and/or aromas grouped together in respective color series and/or from the theoretical colorimetric description and from the test colorimetric descriptions assigned to the test odors grouped together in the respective series of odors, a verification step during which there are identified, from the color series, similar color series with which the odor or the aroma satisfies a first predetermined similarity criterion, and during which the question of whether the odor or the aroma satisfies a second criterion of similarity with a color series taken from the similar color series is verified, and, when the odor or the aroma satisfies the first and the second similarity criteria, the values of the set of sensory descriptors assigned to the odor or to the aroma are subjected, during the second analysis step, to a single second neural network previously subjected to the learning step during which the values of the set of sensory descriptors assigned to the test odors and/or aromas grouped together in said color series with which the odor or the aroma satisfies the second similarity criterion are supplied to it as input, and, when the odor or the aroma satisfies the first similarity criterion but not the second similarity criterion, the values of the set of sensory descriptors assigned to the odor or to the aroma are subjected, during the second analysis step, to a plurality of second neural networks previously subjected to the learning step during which there are supplied to it, as input, the values of the set of sensory descriptors assigned to the test odors and/or aromas grouped together in the color series with which the odor or the aroma satisfies the first similarity criterion, the colorimetric proportions associated with said respective colors being linear combinations of the new colorimetric proportions associated with the respective colors.

Advantageously, the method comprises, prior to the enhancement step, a correction step consisting in updating the theoretical colorimetric description from the values of the set of descriptors associated with the odor or with the aroma and from a global rule making it possible to compute, for at least one color, and from values of the set of sensory descriptors assigned to the aroma or to the odor, a probability of presence, in a colorimetric description associated with these values, of a colorimetric proportion associated with said color, said correction step being followed by a return to the step of computing similarity coefficients.

Advantageously, the step of assigning the test odors and/or aromas a colorimetric description comprising test proportions associated with a set of respective colors, comprises:
- a step of assigning colors, called judged colors, to test odors and/or aromas (by a set of human judges),
- a step of preparing a so-called test colorimetric description of each test odor or aroma comprising test proportions associated with a set of respective colors from the proportion of judges who, out of the judges belonging to another set of judges comprising all or part of said set of judges, have each assigned judged colors to said test odor or aroma.

Advantageously, the test proportions relating to the different colors are determined from the proportion of judges who, out of the judges belonging to the other set of judges, have each assigned judged colors to said aroma or to said odor and from proximity coefficients computed between the judged color and the colors of the set of colors.

Advantageously, the method comprises a step of representing the new odor or the new aroma by means of a chromatic map in which the percentage of the surface of the chromatic map occupied by a color of the set of colors corresponds to the ratio between the proportion associated with said color in the colorimetric description and the sum of the proportions associated with a subset of the set of colors in the colorimetric description, the subset being chosen in such a way that the sum of the proportions associated with the colors that it contains, in the colorimetric description, is at least equal to a predetermined threshold.

Another subject of the invention is a method for transcribing an initial colorimetric description comprising initial colorimetric proportions relating to a set of respective colors into a result physico-chemical description comprising a list of molecules comprising the following steps:
- a second step of physico-chemical analysis of a set of so-called test odors and/or aromas in order to assign, to each test odor or aroma of said set, a so-called test physico-chemical description comprising a so-called test physico-chemical vector comprising test proportions associated with said predetermined set of respective volatile molecules,
- a first step of assigning the test odors and/or aromas respective test colorimetric descriptions comprising so-called test proportions associated with a set of respective colors,
- a second step of assigning a hypothetical colorimetric description comprising hypothetical colorimetric proportions to the set of respective colors to a hypothetical physico-chemical vector comprising hypothetical proportions associated with said set of respective volatile molecules, this second assignment step being performed by means of a first artificial neural network exhibiting a layered architecture, by presenting to it, as input, a hypothetical physico-chemical vector comprising hypothetical proportions associated with said set of respective volatile molecules, said first neural network generating, as output, said hypothetical colorimetric description, said first neural network being previously subjected to a first learning step during which there are supplied to it, as input, physico-chemical vectors associated with the set of test odors and/or aromas, said first learning step being performed in a supervised manner by taking into account the test colorimetric descriptions associated with the set of respective test odors and/or aromas,
- an error computation step in which an error representative of a deviation between the hypothetical colorimetric description and the initial colorimetric description is computed, said error computation step being followed by a step of updating of the hypothetical physico-chemical vector, from the error and the hypothetical physico-chemical vector, and of return to the assignment step as long as the error is greater than a predetermined error threshold, the result physico-chemical description being determined from the hypothetical physico-chemical vector which generates a computation error less than or equal to the error.

Advantageously, the initial description is associated with so-called initial values of a set of sensory descriptors and the test odors and/or aromas are associated with values of said set of sensory descriptors, said set of sensory descriptors comprises at least one sensory descriptor taken from a source of an odor or of an aroma, a wholesomeness index, an agreeability index, a familiarity index, an olfactory note and intensity index, and comprising a preliminary step of determining the hypothetical physico-chemical vector from so-called initial values of the set of sensory descriptors and from values of said set of sensory descriptors associated with the test odor or aroma.

Advantageously, the method comprises, prior to the step of determining the hypothetical physico-chemical vector:
- a step of constructing another global law making it possible to determine, from the values of a set of sensory descriptors associated with an odor or an aroma, the probabilities of presence of the set of respective molecules in the odor or the aroma O being non-zero, this step being performed from test physico-chemical vectors and from the values of the set of sensory descriptors associated with the test odors and/or aromas,
- a step of grouping together of the test odors and/or aromas in a set of color series by similarity of their respective test colorimetric descriptions, the step of determining the hypothetical physico-chemical vector comprising:
- a step of determining probabilities of presence, in the result odor or aroma, of the set of the respective molecules, this step being performed from the initial values of the set of sensory descriptors and from the other global law,
- a step of establishing a list of possible molecules taken from the set of molecules, this list of possible molecules corresponding to the molecules which, out of the molecules of the set of molecules, exhibit a non-zero probability of presence,
- a step of computing correlation coefficients between the initial description and the respective color series from initial values of the set of sensory descriptors and from the values of the set of sensory descriptors associated with the respective test odors and/or aromas as well as from the test and initial colorimetric descriptions,
- a verification step during which there are identified, out of the color series, the color series with which the initial description satisfies a predetermined correlation criterion, this step is performed from similarity coefficients cited in the preceding paragraph,
- a step of preparing the hypothetical physico-chemical vector from the list of possible molecules and from test physico-chemical vectors associated with the test odors and/or aromas included in the color series with which the initial description satisfies the correlation criterion, the hypothetical physico-chemical vector comprising hypothetical proportions associated with the respective possible molecules Mi.

BRIEF DESCRIPTION OF THE DRAWINGS

Other features and advantages of the invention will emerge on reading the following detailed description, given by way of nonlimiting example and with reference to the attached drawings in which.

From one figure to another, the same elements are identified by the same references.

DETAILED DESCRIPTION

Figure 1A:
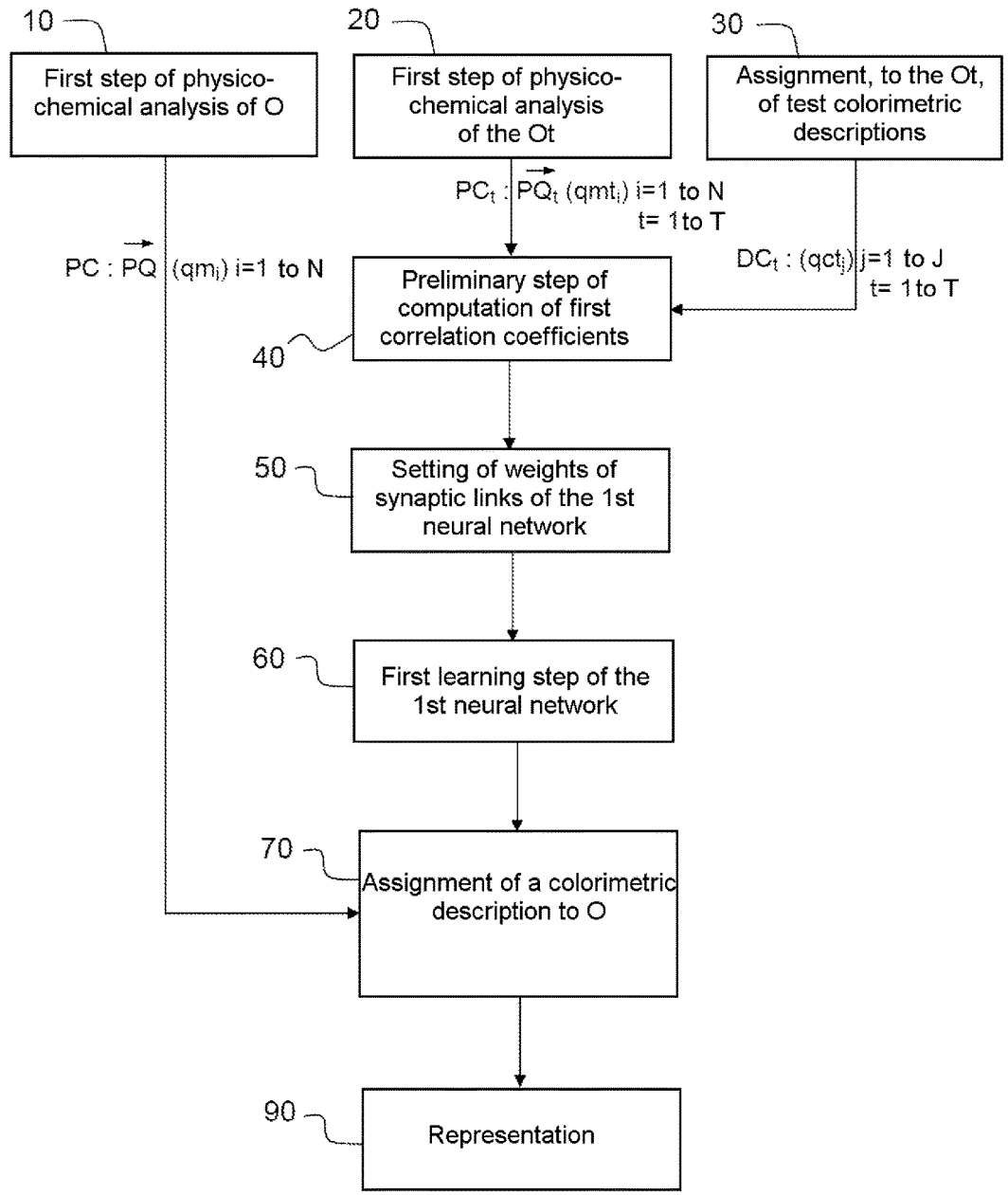
FIG. 1a schematically represents the steps of an exemplary method for transcribing an odor or an aroma into a colorimetric description according to the invention and FIG. 1b represents more specifically the step of assigning a colorimetric description to the odor or to the aroma.

FIG. 1a shows the steps of the method according to the invention for transcribing an odor or an aroma O into a colorimetric description, also called chromatic profile. An odor or an aroma is a set of volatile molecules which can be perceived directly by olfactory means, that is to say by the nose, for an odor, or indirectly, that is to say via the mouth, for an aroma.

This method comprises a step 10 of physico-chemical analysis of the odor or of the aroma O in order to associate with it a physico-chemical description, called physico-chemical description PC, comprising a physico-chemical vector PQ comprising a list of proportions $qm_i$ relating to a predetermined set of respective volatile molecules Mi with i=1 to N in which N is the number of volatile molecules included in a predetermined set of molecules. The proportion of a molecule in the mixture corresponds to its relative proportion in this mixture.

Currently, the number N of molecules is 458, but this number can change.

The sum of the proportions included in each vector corresponds to 1.

This step 10 of physico-chemical analysis is a step that is known to those skilled in the art. It is, for example, performed by means of an electronic nose which is able to pick up the volatile molecules forming an odor or an aroma and to identify them as well as the proportion of the molecules which are included in the mixture of volatile molecules. The electronic nose produces the chromatogram of the odor or of the aroma and identifies, from the chromatogram obtained, the molecules that are present and their respective concentrations (or proportions) in the mixture of volatile molecules originating the odor or the aroma.

An exemplary method of this type is described in the patent application EP1566633.

The physico-chemical description can also comprise a so-called relevance physico-chemical vector PCP comprising relevance indices IPi associated with the set of the respective molecules Mi. A relevance index corresponds to the probability that the molecule is effectively present in the olfactory or aromatic mixture.

This method also comprises a step 20 of physico-chemical analysis of a set of so-called test odors and/or aromas Ot of indices t (with t=1 to T where T is the number of test aromas and/or odors) in order to assign to each test odor or aroma Ot of index t a so-called test physico-chemical description $PC_t$ of index t comprising a test physico-chemical vector $PQ_t$ comprising a list of test proportions $qmt_i$ associated with said predetermined set of respective molecules Mi. These physico-chemical descriptions constitute a first database, called physico-chemical database. The sum of the proportions included in a test physico-chemical vector is equal to 1.

The test physico-chemical description can also comprise a relevance test physico-chemical vector $PCP_t$ comprising relevance test indices $IPt_i$ associated with the set of the respective molecules Mi. A relevance index corresponds to the probability that the molecule is effectively present in the test olfactory or aromatic mixture.

If, during the physico-chemical analysis step, a new molecule is found which is not included in the set of molecules Mi (i=1 to I), it can update the set of molecules such that it incorporates this new molecule. The existing physico-chemical vectors are then updated to incorporate therein the proportions linked to this new molecule, proportions which are zero for the existing vectors. The same applies for the relevance physico-chemical vectors.

The method also comprises a step 30 of assigning the test odors and/or aromas Ot of index t, that is to say to the quantity test physico-chemical vectors PQt of index t, test descriptions DCt comprising test colorimetric proportions $qct_j$ of index t associated with a set of respective colors Cj with j=1 to J where J is the number of colors in the set of colors.

Figure 2:
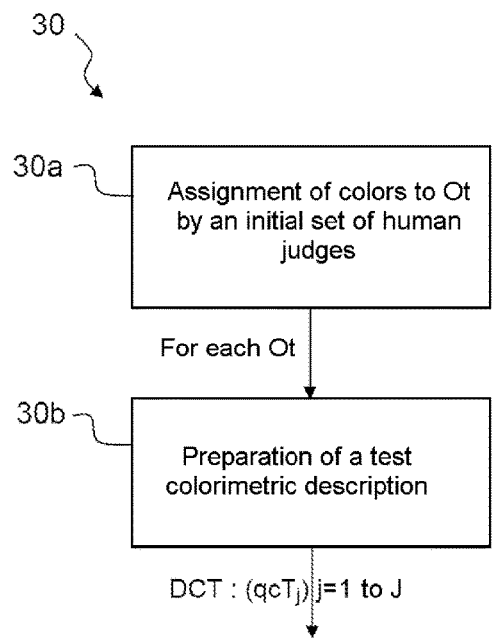
FIG. 2 represents in more detail an exemplary embodiment of the step of assigning test colorimetric descriptions to the set of test odors and/or aromas, FIG. 3 schematically represents a first neural network used in the method according to the invention, FIG. 4 schematically represents an exemplary embodiment of the preliminary step of computing the first correlation coefficients, FIG. 5 schematically represents an exemplary representation of a colorimetric description, FIG. 6 schematically represents another exemplary colorimetric description.

This assignment step 30 is performed partly by human judges. It comprises steps which are represented in FIG. 2.

Each test odor or aroma Ot is presented to a set of human judges. Each judge assigns a color, called judged color, characterized by its coordinates in a three-dimensional reference frame LCH: L (luminosity), C (saturation), H (hue) (step 30a).

From these results, a colorimetric description DCt is prepared for each test odor or aroma Ot, for example, in the form of a test color vector $CT_t$, comprising test colorimetric proportions $qct_j$ associated with a set of respective colors $C_j$ from the proportion of judges, who, out of the judges of another set of judges, made up of all or some of the judges of the set of judges, have each assigned judged colors to said test odor or aroma (step 30b).

The judges can be allowed to chose from a discrete or continuous set of judged colors.

In one embodiment, the set of colors corresponds to all the judged colors that have been assigned by judges to the test odors and aroma. The proportion assigned to a color, for a test odor or aroma, of the set of colors is then equal to the proportion of judges that have assigned said color to the test odor or aroma.

As a variant, the set of colors is a predetermined set of colors spaced apart in the three-dimensional reference frame that can be different from the set of judged colors.

In this case, the test colorimetric proportions $qct_j$ relating to the different colors $C_j$ are determined from the proportion of judges that have each assigned judged colors to said test aroma or said test odor and from proximity coefficients computed between the judged color and the colors of the set of colors.

The other set of judges can be all the judges.

As a variant, the other set comprises only a part of the judges of the set of judges. In this case, the method advantageously comprises a step, not represented, of filtering the set of judges as a function of at least one characteristic of the judges taken from their age, their nationality, their gender, in order to construct the other set of judges. In effect, the characteristics like the age, the nationality or the gender of the judges can have an impact on the colors that they assign to the test odors and/or aromas. This filtering makes it possible to much more accurately target the chromatic profile so as to address different marketing demands. It is possible for example to target a chromatic profile for non-European cultures.

Advantageously, the set of judges comprises a number of judges at least equal to 100. This makes it possible to ultimately obtain a colorimetric description that is the most objective and reproducible possible.

This method also comprises a step 70 of assigning to the odor or the aroma O a colorimetric description DC comprising colorimetric proportions $qc_j$ associated with respective colors $C_j$ of the set of colors comprising J colors (j=1 to J). The sum of the proportions associated with the colors is equal to 1.

This step 70 comprises a first step 71 of assigning (to the odor or to the aroma O a theoretical colorimetric description DCT comprising theoretical colorimetric proportions $qcT_j$ associated with the respective colors Cj of the set of colors comprising J colors (j=1 to J). The sum of the proportions associated with the colors is equal to 1.

Figure 1B:
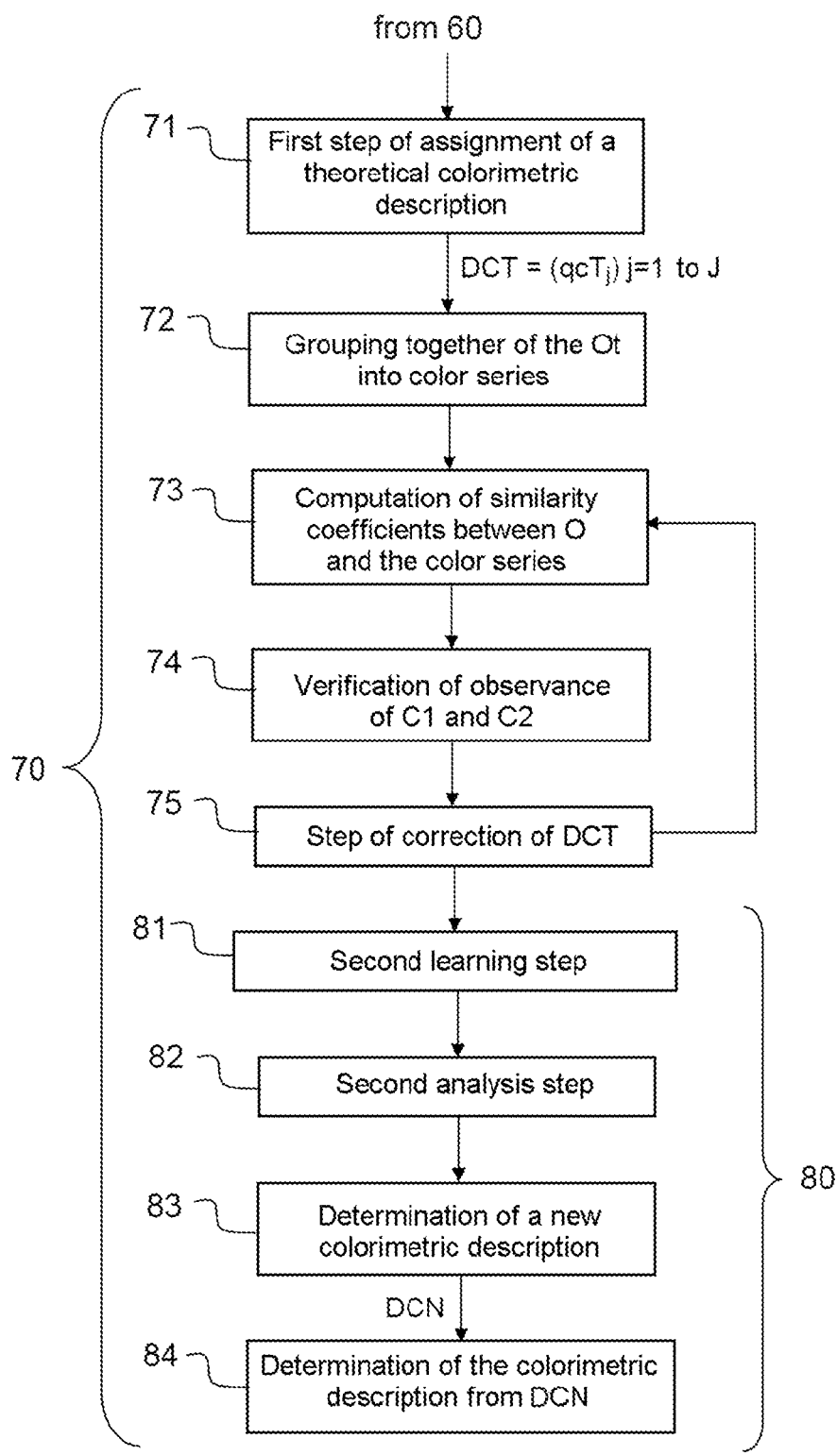
Figure 3:
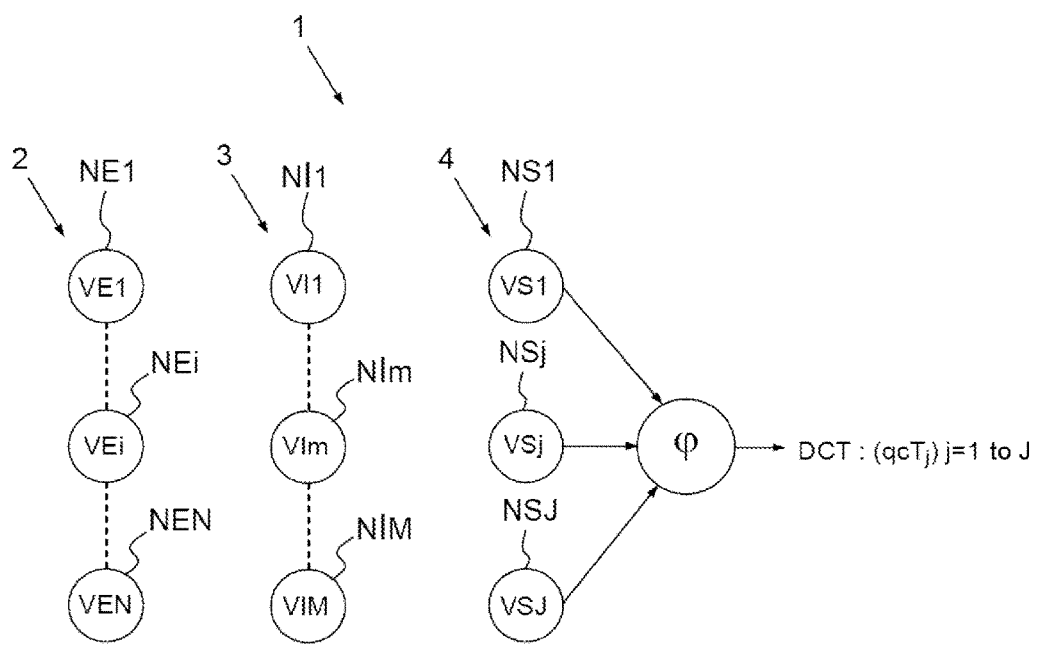

The step 71, represented in FIG. 1b, is performed by means of a first artificial neural network 1 of the multilayer perceptron type, an example of which is represented in FIG. 3. This neural network 1 exhibits a layered architecture comprising successive layers comprising an input layer 2 exhibiting a plurality of input neurons NEi (i=1 to N), the number of which is equal to the number of molecules Mi and supplying, as output, values VEi, called values of the respective input neurons which are equal to the proportions $qc_j$ associated with the respective molecules Mi of a physico-chemical vector PQ which is supplied to it as input.

The artificial neural network 1 further comprises at least one intermediate layer 3 comprising a plurality of intermediate neurons NIm (m=1 to M and M is the number of neurons of the intermediate layer) supplying, as output, values VIm, called values of the respective intermediate neurons. In the example of FIG. 3, the neural network comprises a single intermediate layer.

The neural network 1 further comprises an output layer 4 comprising a plurality of output neurons NSj (j=1 to J), the number of which is equal to the number of colors of the set of colors defined previously and supplying, as output, respective values VSj, called values of the respective output neurons NSj, which are associated with the respective colors Cj.

Each neuron of a layer is linked, by means of synaptic links, to all the neurons of the preceding layer, when it exists, and to all the neurons of the next layer, when it exists. Synaptic weights are assigned to each synaptic link. A synaptic link interlinks two neurons. In other words, in the example of FIG. 3, the first neural network comprises synaptic links linking each input neuron to each intermediate neuron and each intermediate neuron to each output neuron. For more clarity, these synaptic links are not represented in FIG. 3.

The value VIm of an intermediate neuron NIm is equal to a weighted sum of the values of the neurons of the preceding layer, in which the value of each neuron of the preceding layer is weighted by the weights of the synaptic link linking the neuron of the preceding layer and the intermediate neuron NIm concerned.

The value of an output neuron is equal to the weighted sum of the values, called activation values, obtained by applying an activation function fa to the respective values of the neurons of the preceding layer, each activation value being weighted by the weight of the synaptic link linking the output neuron concerned and the neuron of the preceding layer concerned.

The activation function fa is, for example, as follows:

$$fa(VIm) = \frac{1}{1 + e^{-VIm}},$$

regardless of m integer between 1 and M

The values of the neurons of the first neural network will be described more specifically, in a nonlimiting manner, in the case, represented in FIG. 3, in which the first network comprises only a single intermediate layer comprising a number M of intermediate neurons equal to the number J of colors of the set of colors.

The output value VIm of an intermediate neuron NIm is, regardless of m an integer between 1 and M, equal to:

$$VIm = \Sigma_{i=1}^{N} P_{i,m} * VE_i$$

in which $P_{i,m}$ is the weight of the synaptic link linking the neuron NEi and the neuron NIm and in which $VE_i$ is the value of the neuron NEi.

The value VSj of an output neuron is equal to:

$$VSj = \Sigma_{m=1}^{J} K_{m,j} * fa(VIm)$$

in which $K_{m,j}$ is the weight of the synaptic link linking the output neuron NSj and the intermediate neuron NIm.

The values VSj lie within the interval $]-\infty; +\infty[$. Now, the colorimetric proportions $qc_j$ associated with the colors Cj lie between 0 and 1. A nonlinear function $\phi(VSj)$ is therefore applied to the values of the output neurons so as to obtain the proportions $qc_j$.

It is possible, for example, but in a nonlimiting manner, to use the following function:

$$\varphi(VSj) = \frac{t_j}{\sum_{j=1}^{J} t_j} \text{ in which } t_j = VSj$$

if $VSj > 0$ and $0$ if $VSj \le 0$

To determine the weights of the synaptic links of the first neural network 1, the activation functions being set, the first neural network is subjected, prior to the step 70, to a first learning step 60.

The first learning step 60 is performed in a supervised manner by supplying, as input for said first neural network 1, the respective test physico-chemical vectors PQt and by taking into account the test colorimetric descriptions DCt associated with the test odors and/or aromas Ot to which the respective test physico-chemical vectors are assigned.

In other words, the first learning step is performed in such a way that, when a test physico-chemical vector PQt is supplied as input for said first network, a colorimetric description that is as close as possible to the test colorimetric description assigned to said vector is obtained at the output of said first network.

The completion of the learning phase 60 is followed by the step 70 of assigning a colorimetric description DC, to the odor or to the aroma O comprising colorimetric proportions $qc_j$ associated with the colors Cj.

This assignment step 70 comprises a first step 71 of assigning to the odor or to the aroma a theoretical colorimetric description DCT comprising a list of theoretical colorimetric proportions $qcT_j$ associated with the respective colors Cj by supplying the physico-chemical vector PQ as input for the first neural network 1. The output of the first neural network 1 corresponds to the theoretical colorimetric description DCT comprising the list of the theoretical proportions $qcT_j$ associated with the respective colors Cj.

In a first embodiment, the colorimetric description DC is the theoretical colorimetric description DCT.

Advantageously, but not necessarily, the method comprises, prior to the first learning step 60, a fixing step 50 during which weights of first synaptic links linking certain neurons called false neurons two by two are set, in such a way that these weights are not modifiable during the learning step. During the first learning step, the weights of the synaptic links other than the first synaptic links are then set.

The step 50 is performed from first correlation coefficients. Each first correlation coefficient is computed between a molecule of the set of molecules and a color of the set of colors. This step makes it possible to limit the duration of the learning step of the neural network.

The first correlation coefficients are computed in a preliminary step 40 from test physico-chemical vectors and from the test colorimetric descriptions associated with these physico-chemical vectors via the respective test odors or aromas to which they are assigned.

One way of performing this step 40 is described below. In this method, it is presupposed that it is combinations of molecules which are reflected by colors (or combinations of colors).

Figure 4:
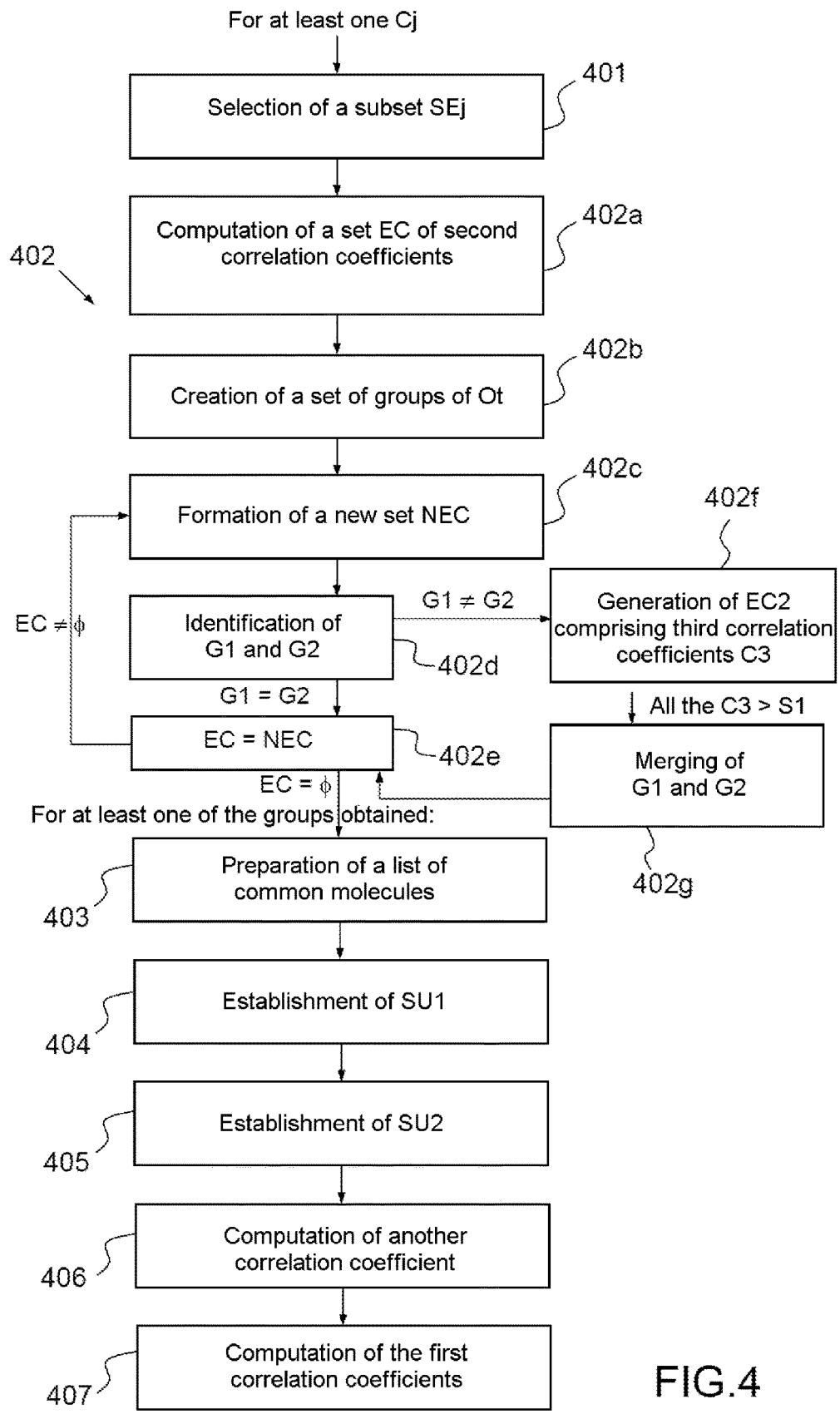

This step 40 is detailed in FIG. 4. It comprises, for at least one color Cj of the set of colors, a step 401 of selecting, from the set of test odors and/or aromas Ot, of a subset SEj of index j of test odors and/or aromas which are associated with test colorimetric descriptions DCt (t=1 to T) exhibiting non-zero test colorimetric proportions for said color of the same index Cj.

The idea is to identify different groups of odors or aromas which exhibit this color in their respective colorimetric descriptions. For example, an odor or an aroma exhibiting an acidulous or lactose note can be associated with the color yellow. Now, these acidulous and lactose notes originate from completely different groups of molecules. In other words, different combinations of molecules can return to the same color. The odors and/or aromas are therefore grouped together according to the similarity of the molecules of which it is composed.

In other words, the step 40 comprises a step 402 of grouping together the test odors and/or aromas of the subset SEj in a set of groups of test odors and/or aromas, such that the physico-chemical vectors PQt of the test odors and/or aromas present in a group exhibit between them higher first correlation coefficients than with the physico-chemical vectors PQt of the test odors and/or aromas present in the other groups of said set of groups. Hereinafter in the text, the notion of grouping together test odors and/or aromas in groups or series should be understood to mean that there are grouped together, in these different groups or series, the test physico-chemical vectors and/or the values of a set of test sensory descriptors and/or the test physico-chemical descriptions which are associated with these test odors and/or aromas.

FIG. 4 shows a nonlimiting example of steps of a method 402 of grouping together test odors and/or aromas present in the subset SEj comprising a number H of test odors and/or aromas.

This method comprises:
- a step 402a of computing second correlation coefficients between each of the physico-chemical vectors associated with the test odors and/or aromas included in the subset SEj and the physico-chemical vectors associated with the other test odors and/or aromas present in the subset SEj so as to obtain a set of correlation coefficients EC comprising the second correlation coefficients,
- a step 402b of creating a first set of groups comprising a number of groups equal to the number H of test odors and/or aromas included in the subset SEj, each group comprising an odor and/or an aroma of said subset,
- a step 402c of forming a new set of correlation coefficients NEC, from the set of correlation coefficients EC, the new set NEC corresponding to the set of correlation coefficients EC in which the highest second correlation coefficient that it contains is eliminated,
- a step 402d of identifying, among said groups, first G1 and second G2 groups comprising the two test odors and/or aromas Ot between which the second correlation coefficient corresponds to the highest second correlation coefficient contained in the correlation set EC,
- if the first G1 and second G2 groups comprise exactly the same test aromas and/or odors, the method comprises a step 402e of updating the set of correlation coefficients EC, the latter being replaced by the new set of correlation coefficients NEC and the method returns to the step 402c of forming a new set of correlation coefficients NEC as long as the correlation set EC comprises at least one second correlation coefficient,
- otherwise, a second set of correlation coefficients EC2 is generated 402f, comprising third correlation coefficients C3 obtained by correlating each physico-chemical vector associated with a test odor or aroma present in the first group G1 with each physico-chemical vector associated with a test odor or aroma present in the second group G2, and if all the third correlation coefficients are above a predetermined first threshold S1 (equal, for example, but in a nonlimiting manner, to 0, 3) the method comprises a step 402h of merging between the first G1 and second G2 groups, in which, in the first set of groups, the first and second groups are replaced by a single group comprising the test odors and/or aromas present in these two groups,
- and then the method returns to step 402e.

At the end of the grouping together step 402, the test odors and/or aromas of the subset SEj have been grouped together as a function of the similarity of the respective physico-chemical vectors.

For at least one of the groups obtained, a list is prepared 403, of common molecules corresponding to the molecules associated with a non-zero test proportion in all the test physico-chemical vectors associated with the test odors and/or aromas grouped together in said group and, for at least one molecule taken from the list of common molecules:

a first series SU1 is established 404, in which the test odors and/or aromas grouped together in said group are arranged in ascending order of the proportion of said molecule in the physico-chemical vectors associated with said test odors and/or aromas, a second series SU2 is established 405, in which the test odors and/or aromas grouped together in said group are arranged in ascending order of the proportion of said color in the colorimetric descriptions associated with said test odors and/or aromas, another correlation coefficient between the first and the second series is computed 406.

In other words, in the series SU1, the test proportions associated with the molecule concerned in the respective physico-chemical vectors associated with the test odors and/or aromas forming said series increase with the order number of the test odors and/or aromas in said series. In the series SU2, the test colorimetric proportions associated with the molecule concerned in the physico-chemical descriptions associated with the respective test odors and/or aromas forming said series increase with the order number of the test odors and/or aromas in said series.

The correlation between the two series SU1, SU2 expresses the probability that the molecule has a statistical relationship with the color concerned, and more specifically that the increase, or the decrease, in the proportion of said molecule in a physico-chemical vector induces an increase, or respectively, a decrease, in the proportion of the color in the colorimetric descriptions. A correlation equal to 1 means that the increase in the proportion of the molecule always corresponds to an increase in the percentage of judges that have selected the color (that is to say the proportion of the color), and a zero correlation indicates to the contrary.

The first correlation coefficient between a molecule of the set of molecules and a color of the set of colors is then computed 407 from other correlation coefficients computed for said molecule and said color. It is, for example, a linear combination of the coefficients of the other correlation coefficients.

Advantageously, but not necessarily, the step 70 of assigning the colorimetric description to the odor concerned comprises a step 80 of enhancing the theoretical colorimetric description from values of a set of sensory descriptors assigned to the odor or to the aroma and to the respective test odors and/or aromas Ot.

The set of sensory descriptors comprises at least one descriptor taken from the source of the odor or the aroma concerned, a wholesomeness index, an agreeability index, its familiarity, an olfactory note, and an intensity index (explains what it corresponds to). The sensory descriptors can take a number of values from predetermined sets of values. For example, the respective indices can take a plurality of values from respective sets of indices.

The method according to the invention comprises, advantageously but not necessarily, prior to the enhancement step 80, a step 72 of grouping together the test odors and/or aromas in a set of series Sb of test odors and/or aromas of order b (b=1 to B) by similarity of their respective test colorimetric descriptions. These series Sb are called color series of order b hereinafter in the text.

In other words, the method comprises a step 72 of grouping together the test odors and/or aromas in color series, such that the test colorimetric descriptions of the test odors and/or aromas present in a first color series exhibit between them higher correlation coefficients than with the test colorimetric descriptions of the test odors and/or aromas present in the other color series of said set of color series.

It is possible to group together, via the step 72, the test odors and/or aromas in series by using the method 402 described previously used to group together test odors and/or aromas according to groups. However, in this method, second, third and other correlation coefficients are computed, not this time between the physico-chemical vectors but between the colorimetric descriptions. Moreover, the starting point is the set of test odors and/or aromas and not a subset.

At the end of this grouping together method, test odors and/or aromas have been grouped together by similarity of the colorimetric descriptions with which they are respectively associated.

The enhancement step 80 also advantageously comprises a step 81 of subjecting at least one second artificial neural network of index b to a learning step consisting in setting synaptic weights for the links between neurons of adjacent layers of said second neural network of index b.

In this step 81, a second neural network of index b exhibits a layered architecture comprising an input layer suitable for receiving values of the set of sensory descriptors associated with the test odors and/or aromas belonging to a series of odors Sg consisting of at least some of the test odors and/or aromas.

The second neural network which receives values of a set of sensory descriptors associated with an odor or an aroma supplies, as output, first Lm, second cm and third mean coordinates Hpm (with p=1 to v an integer generally less than J-2 but which can be greater), in a reference frame L, C, H, of a colorimetric description of this odor or of this aroma. The mean coordinates associated with a colorimetric description comprising proportions $qc_j$ associated with colors Cj of the set of colors comprising J colors (j=1 to J) are given by the following formulae:

$$Lm = \sum_{j=1}^{J} Lj * qc_j$$

in which Lj is the coordinate of the color Cj on the axis L. Lj is between 0 and 100.

$$cm = \sum_{j=1}^{J} cj * qc_j$$

in which cj is the coordinate of the color Cj on the axis C. cj is between 0 and 181.

$$Hpm = \sum_{j=1}^{J} PHpj * qc_j$$

in which PHpj is the weight of index p of the color Cj in the space H and p=1 to v. PHpj is between 0 and 360.

In the space H of the hues lying between 0 and 360°, the following are noted:

$$H_1 = 0 \text{ or } 360 \text{(angular coordinates)}, H_2 = 360/v,$$
$$H_3 = 2*360/v,$$

$$H_v = (v-1)*360/v$$

For a given color, there is always a value x such that a hue Hx bears out:

$$x \in \{1, 2, \ldots v\} \text{ such that } H_x \leq H < H_{x+1}, \text{ it must be noted that } (H_{v+1} = H_1)$$

And there is always a value a between 0 and 1 such that:

$$H_x * a + H_{x+1} * (1-a) = H$$

For each color of index j, the following then applies $$PH_{xj} = a \text{ and } PH_{(x+1)j}$$

and all the other coordinates $PH_{pj}$ of index p different from x and x+1 are zero.

The PH are an expression of H which is continuous.

The mean coordinates Lm, cm and Hpm associated with a chromatic map are influenced by the values of the sensory descriptors of the corresponding odor.

In a color series Sb, the impact of the values of the sensory descriptors on the mean coordinates follows a local rule that can be determined using at least one second neural network in which the inputs are values of a set of sensory descriptors associated with an odor or an aroma and the outputs are the mean coordinates associated with this aroma or with this odor in the reference frame L, H, C.

A detailed description of the second neural network which exhibits an architecture similar to that of the first neural network is not described in detail here. The activation function of these neural networks is the same as that of the first neural network.

The learning step 81 of a second neural network is performed in a supervised manner by supplying, as input for said second neural network, the values of the sets of sensory descriptors associated with respective test odors and/or aromas of a color series concerned Sb and by taking into account colorimetric descriptions associated with the respective test odors and/or aromas of these test odors and/or aromas.

The method further comprises a second step 82 of analysis of the values of the set of sensory descriptors associated with the odor or the aroma to which a colorimetric description is to be assigned. During this step 82, the values of the set of descriptors associated with the odor or the aroma are supplied as input for said second neural network, each second neural network supplying target mean coordinates, in the reference frame L, C, H, of a target colorimetric description associated with the odor or with the aroma concerned.

A second neural network of index b supplies the following target mean coordinates Lmbutb, cmbutb, Hpmbutb (p=1 to v).

The colorimetric description is generated from the theoretical description and from the target mean coordinates obtained.

It is obtained as follows.

From the target mean coordinates of index b: Lmbutb, cmbutb, Hpmbutb, obtained from a second neural network of index b, in a step 83, a new colorimetric description DCN is computed comprising new colorimetric proportions qcnbj which observe the equations satisfied by Lmbutb, cmbutb, Hpmbutb, namely:

$$Lmbutb = \sum_{j=1}^{J} Lj * qcnb_j$$

$$cmbutb = \sum_{j=1}^{J} cj * qcnb_j,$$

$$Hpmbutb = \sum_{j=1}^{J} PHpj * qcnb_j \text{ with } p=1 \text{ to } v,$$

and which minimize, for at least one color index j, the absolute value $|qcnb_j - qcTb_j|$ of the difference between the new proportion of index b and the theoretical proportion of index b.

Advantageously, the method comprises, prior to the enhancement step 80, a step 73 of computing coefficients of similarity of between the odor or the aroma and respective color series Sb, from values of the set of sensory descriptors assigned to said odor or to the aroma and from values of the set of sensory descriptors assigned to the test odors and/or aromas grouped together in the respective series of odors and/or from the theoretical colorimetric description and from test colorimetric descriptions assigned to the test odors of the respective series of odors.

The method then comprises a verification step 74 in which there are identified, from the series of colors, color series called similar color series, with which the odor or the aroma concerned bears out a first predetermined similarity criterion C1 consisting for example in identifying the color series with which the odor or the aroma exhibits a similarity coefficient above a second predetermined threshold S2.

This step 74 also comprises a step consisting in verifying whether the odor or the aroma bears out a second similarity criterion C2 with a particular color series taken from the similar color series, by verifying, for example, whether the difference between the highest similarity coefficient taken from the similarity coefficients computed with the series identified in the preceding step and the similarity coefficient which is just below the latter is above a third predetermined threshold S3.

If it is, in the step 82, the values of the set of sensory descriptors assigned to the odor or to the aroma are submitted to a single second neural network previously subjected to a learning step 81 during which there were supplied to it, as input, the values of the set of sensory descriptors associated with the test odors and/or aromas grouped together in the color series of index b which generated, with the odor or the aroma, the highest similarity coefficient (that is to say the one with which the odor or the aroma bears out the second similarity coefficient). The output of the second neural network provides target mean coordinates of order b in the reference frame LCH: Lmbutb, cmbutb, Hpmbutb. In a step 84, the colorimetric description is then computed from the new colorimetric description. The colorimetric description is the new colorimetric description which comprises new proportions $qcn_j$ associated with colors $C_j$ which bear out the following equations:

$$Lmbutb = \sum_{j=1}^{J} Lj * qcn_j$$

$$cmbutb = \sum_{j=1}^{J} cj * qcn_j,$$

$$Hpmbutb = \sum_{j=1}^{J} PHpj * qcn_j$$

and minimize, for at least one color Cj, the absolute value $|qcn_j - qct_j|$ of the difference between the new proportion of order b and the theoretical proportion.

When the odor or the aroma concerned does not exhibit any special compatibility, this means that the odor or the aroma concerned can be compatible with a plurality of color series. The odor or the aroma bears out the first criterion of similarity with a plurality of color series but does not bear out the second criterion of similarity with any color series.

In this case, in the step 82, the values of the set of sensory descriptors assigned to the odor or to the aroma are submitted to a plurality of second neural networks of order b' (with b'=1 to B', where B' is equal to the number of color series identified in the step 73b).

Each neural network of order b', with b'=1 to B', is previously subjected to a learning step 81 during which the values of the set of sensory descriptors associated with the series with which the odor or the aroma concerned bears out the first similarity criterion are supplied to it as input.

In the analysis step 82, each neural network of index b', with b'=1 to B', receives as input the values of the set of sensory descriptors associated with the odor or the aroma concerned so as to obtain target mean coordinates of order b' in the reference frame LCH Lmbutb', cmbutb', Hpmbutb', and obtain a new colorimetric description of order b' comprising new colorimetric proportions of order b' $qcnb'_j$ for the colors of index j which bear out the following equations:

$$Lmbutb' = \sum_{j=1}^{J} Lj * qcnb'_j$$

$$cmbutb' = \sum_{j=1}^{J} cj * qcnb'_j,$$

$$Hpmbutb' = \sum_{j=1}^{J} PHpj * qcnb'_j$$

and which minimize, for at least one color Cj, the absolute value j $|qcnb'_j - qct_j|$ of the difference between the new proportion of order b' and the theoretical proportion computed for the color of index j.

It is considered that the odor or the aroma concerned is a linear combination of odors of different series.

The colorimetric description associated with the odor or the aroma concerned comprises proportions $qc_j$ associated with respective colors $C_j$, the colorimetric proportions associated with the colors being linear combinations of the new colorimetric proportions associated with the respective colors. The colorimetric proportion associated with a color of index j is equal to a linear combination of the new proportions of order b' $qcnb'_j$ and of index j, that is to say:

$$qc_j = \sum_{b'=1}^{B'} qcnb'_j * kb' o\grave{u} \sum_{b'=1}^{B'} kb' = 1$$

In other words, the colorimetric description obtained is a linear combination of the new colorimetric descriptions obtained for the indices b' for b'=1 to B'.

When the odor or the aroma concerned is not compatible with any color series, that is to say when the first similarity criterion C1 is not borne out, either the odor cannot be analyzed by means of the current databases (the only solution is to enrich the database with new test odors and/or aromas), or the theoretical colorimetric description is errored.

In the latter case, the method comprises, prior to the enhancement step, a step 75 of correcting the theoretical colorimetric description DCT from a global rule and from values of the set of sensory descriptors assigned to the odor or the aroma concerned.

Knowing the sensory descriptors of the odor, it is possible to obtain the probabilities of occurrence of each of the colors Cj in the colorimetric descriptions of the test odors with each of these descriptors.

It is possible to construct, from the values of the set of sensory descriptors and the test colorimetric descriptions associated with the respective test odors and/or aromas, a global rule making it possible to compute, for at least one color, from values of a set of sensory descriptors comprising at least one sensory descriptor, a probability of presence, in a colorimetric description associated with these values, of a non-zero colorimetric proportion associated with said color.

The correction step therefore comprises:
a step of computing, for each color of the set of colors, from the values of the set of sensory descriptors associated with the odor or the aroma concerned, and from the global rule, the probability that the colorimetric proportion associated with said color is non-zero,
a step of updating the theoretical colorimetric description, by canceling the proportions associated with the colors for which the probability that the proportion associated with this color is non-zero is lower than a fourth predetermined threshold, and of readjustment of the other proportions by retaining the same ratio between these other proportions and in such a way that the sum of these other readjusted proportions is equal to 1.

On completion of this correction step, there is a return to the step 73 of computing coefficients of similarity between the odor and the color series.

The method according to the invention makes it possible to transcribe, automatically, objectively and reproducibly, an odor or an aroma into a colorimetric description from associations between colors and odors which are made previously. The fact of using correlation coefficients between colors or combinations of color and molecules and/or combinations of molecules to perform this transcription makes it possible to obtain highly reliable results. This also makes it possible to be able to transcribe an odor or an aroma which does not form part of the odor and/or aroma samples which have previously been tested by judges. Moreover, it makes it possible to assign colorimetric descriptions to complex odors or aromas deriving from a significant number of volatile molecules by having performed prior tests among the judges on simple odors and/or aromas deriving from a small number of volatile molecules. The neural networks, through their learning and classification capabilities, are particularly suited to problems of a statistical nature like that of the invention.

Figure 5:
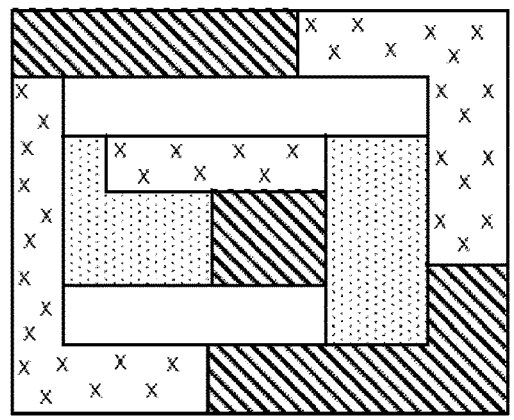

The method according to the invention further, advantageously, comprises a step 90 of representing the odor or of the aroma O by means of a chromatic map or profile in which the percentage of the surface of the chromatic map occupied by a color Cj of the set of colors corresponds to the ratio between the proportion associated with said color $qc_j$ in the colorimetric description and the sum of the proportions associated with a subset of the set of colors in the colorimetric description, the subset being chosen in such a way that the sum of the proportions associated with the colors that it contains, in the colorimetric description, is at least equal to a predetermined threshold which is, for example, equal to 95%. If the threshold is 100%, the subset is the set of colors. In FIG. 5, an exemplary chromatic map 100 is represented comprising a plurality of areas of different colors. The areas exhibiting different colors are represented by different patterns. The proportion of the surface of the chromatic map exhibiting a determined color, that is to say associated with a pattern, is equal to the proportion associated with that color in the colorimetric description. In FIG. 5, the chromatic map exhibits areas associated with 4 different colors (or patterns). The colorimetric description therefore comprises non-zero proportions for only 4 colors.

In this example, the chromatic map comprises a plurality of areas associated with each color, but it would be possible to provide a single area, on the chromatic map, exhibiting a color taken from the colors exhibiting non-zero proportions in the colorimetric description.

It would also be possible to provide a chromatic map in the form of a circular diagram or any other form provided that it has at least one uniform area exhibiting a determined color. The proportion of the surface of the chromatic map occupied by the area or areas exhibiting a determined color is equal to the proportion associated with that color in the colorimetric description.

Figure 6:
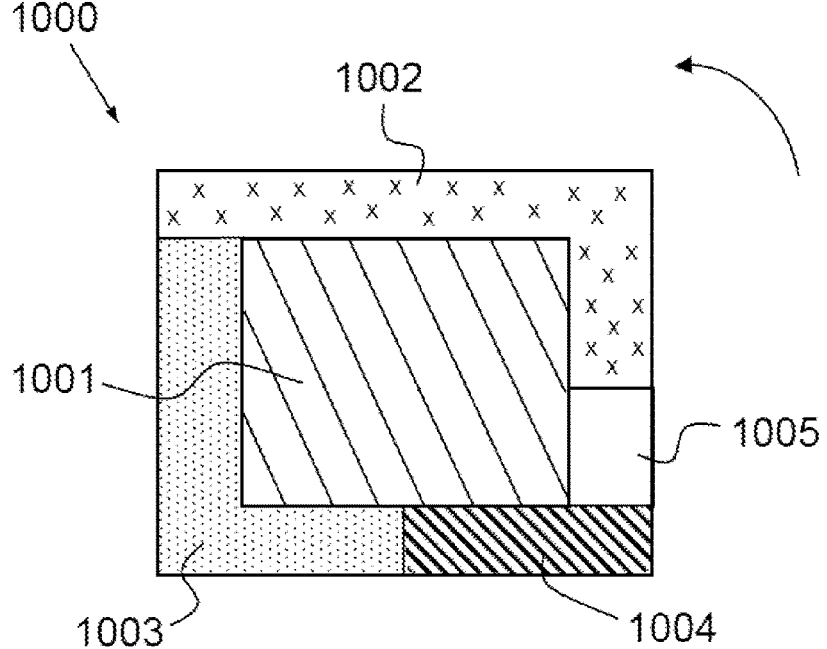

One way of constructing a chromatic map comprising a central area and a peripheral area surrounding the central area can consist in showing, at the center of the map, the color exhibiting the greatest proportion at the center of the map and in showing the other colors around the first by revolving around the central area in a direction (clockwise or counter-clockwise) in an order corresponding to the descending order of the proportions associated with said colors. The respective proportions of the surface of the map occupied by the respective colors correspond to the respective proportions of said colors in the colorimetric description. FIG. 6 represents an exemplary representation 1000 of this type, produced by revolving in the counter-clockwise direction, represented by the arrow, in which the color 1001 exhibits the greatest proportion in the colorimetric description and occupies the greatest proportion of the surface of the map 1000. The colors 1002, 1003, 1004 and 1005 occupy increasingly small respective proportions of the surface of the map 1000.

Advantageously, the first step of physico-chemical analysis comprises a step of assigning a first physico-chemical vector comprising proportions associated with a first set of respective molecules, comprising the molecules of the set of molecules and additional molecules. This first step further comprises a filtering step consisting in constructing the physico-chemical vector from the first physico-chemical vector.

The same may apply for the second analysis step. In other words, this second step can comprise a step of assigning a first test physico-chemical vector to each test odor or aroma comprising test proportions associated with a first set of respective molecules, comprising the molecules of the set of molecules and additional molecules, as well as a filtering step consisting in constructing each test physico-chemical vector associated with an odor or an aroma from the first test physico-chemical vector associated with the odor or the aroma.

Another subject of the invention is a method for transcribing, into a result physico-chemical description comprising a list of molecules, an initial description comprising an initial colorimetric description DCI comprising initial proportions $qcl_j$ associated with a set of respective colors Cj, and possibly values, called initial values, of a set of sensory descriptors (as described previously). These initial values correspond to sensory notes relating to the odor or the aroma that is being researched.

This method comprises a step of physico-chemical analysis of a set of so-called test odors and/or aromas Ot in order to assign, to each test odor or aroma Ot of said set, a so-called test physico-chemical description $PC_t$ comprising a so-called test physico-chemical vector $PQ_t$ comprising test proportions $qmt_i$ associated with said predetermined set of respective volatile molecules M corresponding to the step 20 described previously.

This method also comprises a first step of assigning to the test odors and/or aromas Ot respective test colorimetric descriptions DCt comprising so-called test proportions $qct_j$ associated with a set of respective colors Cj. This step corresponds to the step 30 described previously and can be performed in accordance with the steps 30a and 30b.

This method also comprises a second step of assigning a hypothetical colorimetric description comprising hypothetical colorimetric proportions qcHj associated with the set of respective colors Cj to a hypothetical physico-chemical vector PCH comprising hypothetical proportions $qmH_j$ associated with said set of respective volatile molecules Mi, this assignment step being performed by means of the first neural network 1 described previously. This neural network has previously undergone a first learning phase identical to the step 60 described previously, performed in such a way as to set the weights of the neural network.

The second assignment step is performed by presenting, as input for the first neural network, a hypothetical physico-chemical vector PCH associated with said set of respective volatile molecules Mi, said first neural network 1 generating, as output, said hypothetical colorimetric description DCH.

The method also comprises a step of error computation in which an error representative of a deviation between the hypothetical colorimetric description and the initial colorimetric description is computed, said error computation step being followed by a step of updating the hypothetical physico-chemical vector PCH, from the error and the hypothetical physico-chemical vector (so as to generate a reduction of this error upon the presentation of the updated hypothetical physico-chemical vector as input for the first neural network) and of return to the assignment step as long as the error is above a predetermined error threshold, the list of the molecules being determined from the hypothetical physico-chemical vector which generates a computation error less than or equal to the error.

There are a number of ways of determining a hypothetical physico-chemical vector.

A first way can consist in using so-called initial values of a set of sensory descriptors.

The set of sensory descriptors is a set as described previously.

The method advantageously comprises, prior to the step of determining the hypothetical physico-chemical vector:
  a step of constructing another global law that makes it possible to determine, from values of a set of sensory descriptors associated with an odor or an aroma O, the probabilities of presence, that is to say the probabilities that the respective proportions associated with a set of respective molecules in the mixture of volatile molecules originating the odor or aroma O are non-zero, this step being performed from test physico-chemical vectors and values of the set of sensory descriptors associated with the test odors and/or aromas,
  a step of grouping together the test odors and/or aromas in a set of color series Sb of order b by similarity of their respective test colorimetric descriptions corresponding to the respective step 72.

The step of determining the hypothetical physico-chemical vector is performed notably from the so-called initial values of a set of sensory descriptors, the global law, the values of said set of sensory descriptors associated with the test odors and/or aromas, the colorimetric descriptions associated with the test odors and/or aromas and the test physico-chemical vectors.

This step comprises:
  a step of determining the probabilities of presence, in the result odor or aroma, of the set of the respective molecules, this step being performed from initial values of the set of sensory descriptors and from the other global law,
  a step of establishing a list of possible molecules taken from the set of molecules, this list of possible molecules corresponding to the molecules which, out of the molecules of the set of molecules, exhibit a non-zero probability of presence, a step of computing correlation coefficients between the initial description DI and the respective color series from the initial values of the set of sensory descriptors and the values of the set of sensory descriptors associated with the respective test odors and/or aromas as well as from the test and initial colorimetric descriptions), a verification step in which, from among the color series, the color series with which the initial description bears out a predetermined correlation criterion are identified, this step is performed from the similarity coefficients cited in the preceding paragraph, a step of preparing the hypothetical physico-chemical vector from the list of possible molecules and from the test physico-chemical vectors associated with the test odors and/or aromas included in the color series with which the initial description bears out the correlation criterion. The hypothetical physico-chemical vector comprises hypothetical proportions $qmH_i$ associated with the respective possible molecules Mi.

The first hypothetical physico-chemical vector that is presented to the first neural network is critical for the system to ultimately propose an acceptable hypothetical physico-chemical vector.

It may be necessary to present a plurality of hypothetical physico-chemical vectors before obtaining an acceptable solution. To this end, the error computation step is followed, for example when the error is above a predetermined threshold, by a step of returning to the step of establishing a new hypothetical physico-chemical vector followed by the step of presenting the latter to the first neural network.

In an extreme condition, in which no color series correlated with the initial description is found, it is possible to establish a third neural network of the multilayer perceptron type comprising an input layer suitable for receiving color coordinates in a reference frame LCH and sensory descriptors, and for supplying, as output, a physico-chemical vector.

The output supplied by this network can be used as hypothetical physico-chemical vector. This method presents an increased risk of error because of the size difference of the two types of physico-chemical and sensory data.

This second method makes it possible to propose a list of olfactory molecules corresponding to predetermined sensory notes. These molecules will thus be able to be arranged by a flavor chemist or a perfumer in order to deliver a perfume matched to a colored chart, for example.

Advantageously, at least some of the steps 40, 50, 60, 70, and, preferably, all these steps, are performed by means of a computer. Advantageously, the step 90 is controlled by a computer. Advantageously, in the second method, at least one of the following steps, and preferably all the following steps, are implemented by a computer: the second step of colorimetric description assignment, the first learning step, the error computation step, the step of updating the physico-chemical vector. Advantageously, the preliminary step of determining the hypothetical physico-chemical vector is implemented by a computer. Advantageously, the step of constructing another global law and the step of grouping together the test odors and/or aromas are implemented by a computer.

The invention claimed is:

1. A method for transcribing an odor or an aroma into a colorimetric description comprising the following steps:
   a first step of physico-chemical analysis of said odor or of said aroma in order to associate with it a physico-chemical description comprising a physico-chemical vector, comprising proportions associated with a predetermined set of respective volatile molecules,
   a second step of physico-chemical analysis of a set of so-called test odors and/or aromas in order to assign to each test odor or aroma of said set a so-called test physico-chemical description comprising a so-called test physico-chemical vector comprising test proportions associated with said predetermined set of respective volatile molecules,
   a step of assigning to the test odors and/or aromas respective test colorimetric descriptions comprising so-called test proportions associated with a set of respective colors,
   a step of assigning to the odor or to the aroma a colorimetric description comprising proportions associated with said respective colors, said assignment step comprising a first step of assigning to the odor or to the aroma a theoretical colorimetric description comprising theoretical colorimetric proportions associated with said respective colors, this first assignment step being performed by means of a first artificial neural network exhibiting a layered architecture, by presenting to it, as input, the physico-chemical vector, said first neural network, as output, said theoretical colorimetric description, said first neural network being previously subjected to a first learning step during which there are supplied to it, as input, physico-chemical vectors associated with the set of test odors and/or aromas, said first learning step being performed in a supervised manner by taking into account the test colorimetric descriptions associated with the respective set of test odors and/or aromas.

2. The transcription method as claimed in claim 1, comprising, prior to the first learning step, a fixing step during which weights of first synaptic links linking neurons of said neural network two by two are set such that the weights associated with the first synaptic links are not modifiable during the learning step.

3. The transcription method as claimed in claim 2, in which the fixing step is performed from first correlation coefficients, each first correlation coefficient being computed between a molecule of the set of molecules and a color of the set of colors, computed in a preliminary step from test physico-chemical vectors and colorimetric descriptions associated with the test odors and/or aromas to which said physico-chemical vectors are assigned.

4. The transcription method as claimed in claim 3, in which the preliminary step comprises for at least one color of index j:
   a step of selecting, from the set of test odors and/or aromas, a subset of index j of test odors and/or aromas which are associated with test colorimetric descriptions exhibiting non-zero proportions for said color of index j,
   a first step of grouping together test odors and/or aromas of the subset in a set of groups of test odors and/or aromas, such that the physico-chemical vectors associated with the test odors and/or aromas present in a group exhibit, between them, greater first correlation coefficients than with the physico-chemical vectors associated with the test odors and/or aromas present in the other groups of said set of groups,
   and for at least one of said groups,
   a step of preparing a list of common molecules corresponding to the molecules for which the test proportion is non-zero in all the test physico-chemical vectors associated with the test odors and/or aromas grouped together in said group, and, for at least one molecule taken from the list of common molecules, a step during which a first series is established, in which the test odors and/or aromas grouped together in said group are arranged in ascending order of the proportion of said molecule in the test physico-chemical vectors associated with said test odors and/or aromas, a step during which a second series is established, in which the test odors and/or aromas grouped together in said group are arranged in ascending order of the proportion of said color in the colorimetric descriptions associated with said test odors and/or aromas, a step of computing another correlation coefficient between the first series and the second series, a step of computing at least one first correlation coefficient between a molecule of the set of molecules and a color of the set of colors from the other correlation coefficients computed for said molecule and said color.

5. The transcription method as claimed in claim 1, in which the colorimetric description is the theoretical colorimetric description.

6. The transcription method as claimed in claim 1, in which the step of assigning the colorimetric description comprises a step of enhancing the theoretical colorimetric description from values of a set of sensory descriptors assigned to the odor or to the aroma and to respective test odors and/or aromas so as to obtain said colorimetric description, the set of sensory descriptors comprising at least one sensory descriptor taken from a source of an odor or of an aroma, a wholesomeness index, an agreeability index, a familiarity index, an olfactory note, and an intensity index.

7. The transcription method as claimed in claim 6, in which the enhancement step comprises:

a step of submitting at least one second artificial neural network of index b to a second learning step, a second neural network exhibiting a layered architecture comprising an input layer suitable for receiving values associated with the set of sensory descriptors and supplying as output first Lm, second cm and third Hpm mean coordinates, in which p is an integer ranging from 1 to v an integer, in a colorimetric reference frame called L, C, H, said second neural network receiving, during the second learning step, values of the set of sensory descriptors associated with the test odors and/or aromas present in a color series made up of at least a part of the test odors and/or aromas of the set of test odors and/or aromas, a second step of analysis of the odor or of the aroma by supplying the values of the set of sensory descriptors as input for said second neural network of index b which supplies, as output, first Lmbutb, second cmbutb and third Hpmbutb target mean coordinates of index b in reference frame L, H, C, of a target colorimetric description associated with the odor or with the aroma concerned, a step computing a new colorimetric description comprising new proportions $qcnb_j$ which observe, regardless of the value of j between 1 and J, the following equations:

$$Lmbutb = \sum_{j=1}^{J} Lj * qcnb_j$$

$$cmbutb = \sum_{j=1}^{J} cj * qcnb_j,$$

$$Hpmbutb = \sum_{j+1}^{J} PHpj * qcnb_j$$

with p an integer ranging from 1 to v and v an integer, in which Lj, cj and PHpj are the respective coordinates of the color Cj of index j in the reference frame L, H, C, and which minimize, for at least one color Cj, the absolute value $$|qcnb_j - qcTb_j|$$

of the difference between the new proportion of order b and the theoretical proportion of order b.

8. The transcription method as claimed in claim 6, comprising, prior to the enhancement step, a second step of grouping together test odors and/or aromas belonging to the set of test odors and/or aromas in a set of series, called color series, by similarity of the test colorimetric descriptions which are assigned to them.

9. The transcription method as claimed in claim 8, comprising:

a step of computing coefficients of similarity between the odor and the respective color series, from values of the set of sensory descriptors assigned to the odor or to the aroma and to the test odors and/or aromas grouped together in respective color series and/or from the theoretical colorimetric description and from the test colorimetric descriptions assigned to the test odors grouped together in the respective series of odors, a verification step during which there are identified, from the color series, similar color series with which the odor or the aroma satisfies a first predetermined similarity criterion, and during which the question of whether the odor or the aroma satisfies a second criterion of similarity with a color series taken from the similar color series is verified, and, when the odor or the aroma satisfies the first and the second similarity criteria, the values of the set of sensory descriptors assigned to the odor or to the aroma are subjected, during the second analysis step, to a single second neural network previously subjected to the learning step during which the values of the set of sensory descriptors assigned to the test odors and/or aromas grouped together in said color series with which the odor or the aroma satisfies the second similarity criterion are supplied to it as input, and, when the odor or the aroma satisfies the first similarity criterion but not the second similarity criterion, the values of the set of sensory descriptors assigned to the odor or to the aroma are subjected, during the second analysis step, to a plurality of second neural networks previously subjected to the learning step during which there are supplied to it, as input, the values of the set of sensory descriptors assigned to the test odors and/or aromas grouped together in the color series with which the odor or the aroma satisfies the first similarity criterion, the colorimetric proportions associated with said respective colors being linear combinations of new colorimetric proportions associated with the respective colors.

10. The transcription method as claimed in claim 6, comprising, prior to the enhancement step, a correction step consisting in updating the theoretical colorimetric description from the values of the set of descriptors associated with the odor or with the aroma and from a global rule making it possible to compute, for at least one color, and from values of the set of sensory descriptors assigned to the aroma or to the odor, a probability of presence, in a colorimetric description associated with these values, of a colorimetric proportion associated with said color, said correction step being followed by a return to the step of computing similarity coefficients.

11. The transcription method as claimed in claim 1, in which the step of assigning to the test odors and/or aromas a colorimetric description comprising test proportions associated with a set of respective colors, comprises:
- a step of assigning colors, called judged colors, to test odors and/or aromas by a set of human judges,
- a step of preparing a so-called test colorimetric description of each test odor or aroma comprising test proportions associated with a set of respective colors from the proportion of judges who, out of the judges belonging to another set of judges comprising all or part of said set of human judges, have each assigned judged colors to said test odor or aroma.

12. The transcription method as claimed in claim 11, in which the test proportions relating to the different colors are determined from the proportion of judges who, out of the judges belonging to the other set of judges, have each assigned judged colors to said aroma or to said odor and from proximity coefficients computed between the judged color and the colors of the set of colors.

13. The transcription method as claimed in claim 1, comprising a step of representing the new odor or of the new aroma by means of a chromatic map in which the percentage of the surface of the chromatic map occupied by a color of the set of colors corresponds to the ratio between the proportion associated with said color in the colorimetric description and the sum of the proportions associated with a subset of the set of colors in the colorimetric description, the subset being chosen in such a way that the sum of the proportions associated with the colors that it contains, in the colorimetric description, is at least equal to a predetermined threshold.

14. A method for transcribing an initial colorimetric description comprising initial colorimetric proportions relating to a set of respective colors into a result physico-chemical description comprising a list of molecules comprising the following steps:
- a second step of physico-chemical analysis of a set of so-called test odors and/or aromas in order to assign, to each test odor or aroma of said set, a so-called test physico-chemical description comprising a so-called test physico-chemical vector comprising test proportions associated with said predetermined set of respective volatile molecules,
- a first step of assigning to the test odors and/or aromas respective test colorimetric descriptions comprising so-called test proportions associated with a set of respective colors,
- a second step of assigning of a hypothetical colorimetric description comprising hypothetical colorimetric proportions to the set of respective colors, to a hypothetical physico-chemical vector comprising hypothetical proportions associated with said set of respective volatile molecules, this second assignment step being performed by means of a first artificial neural network exhibiting a layered architecture, by presenting to it, as input, a hypothetical physico-chemical vector comprising hypothetical proportions associated with said set of respective volatile molecules, said first neural network generating, as output, said hypothetical colorimetric description, said first neural network being previously subjected to a first learning step during which there are supplied to it, as input, physico-chemical vectors associated with the set of test odors and/or aromas, said first learning step being performed in a supervised manner by taking into account the test colorimetric descriptions associated with the set of respective test odors and/or aromas,
- an error computation step in which an error representative of a deviation between the hypothetical colorimetric description and the initial colorimetric description is computed, said error computation step being followed by a step of updating the hypothetical physico-chemical vector, from the error and the hypothetical physico-chemical vector, and of return to the assignment step as long as the error is greater than a predetermined error threshold, the result physico-chemical description being determined from the hypothetical physico-chemical vector which generates a computation error less than or equal to the error.

15. The transcription method as claimed in claim 14, in which the initial description is associated with so-called initial values of a set of sensory descriptors and the test odors and/or aromas are associated with values of said set of sensory descriptors, said set of sensory descriptors comprises at least one sensory descriptor taken from a source of an odor or of an aroma, a wholesomeness index, an agreeability index, a familiarity index, an olfactory note and an intensity index, and comprising a preliminary step of determining the hypothetical physico-chemical vector from so-called initial values of the set of sensory descriptors and from values of said set of sensory descriptors associated with the test odor or aroma.

16. The transcription method as claimed in claim 15, comprising, prior to the step of determining the hypothetical physico-chemical vector:
- a step of constructing another global law making it possible to determine, from the values of a set of sensory descriptors associated with an odor or an aroma, the probabilities of presence of the set of respective molecules in the odor or the aroma being non-zero, this step being performed from test physico-chemical vectors and from the values of the set of sensory descriptors associated with the test odors and/or aromas,
- a step of grouping together the test odors and/or aromas in a set of color series by similarity of their respective test colorimetric descriptions, the step of determining the hypothetical physico-chemical vector comprising:
- a step of determining probabilities of presence, in the result odor or aroma, of the set of the respective molecules, this step being performed from the initial values of the set of sensory descriptors and from the other global law,
- a step of establishing a list of possible molecules taken from the set of molecules, this list of possible molecules corresponding to the molecules which, out of the molecules of the set of molecules, exhibit a non-zero probability of presence,
- a step of computing correlation coefficients between the initial description and the respective color series from initial values of the set of sensory descriptors and from the values of the set of sensory descriptors associated with the respective test odors and/or aromas as well as from the test and initial colorimetric descriptions,
- a verification step during which there are identified, out of the color series, the color series with which the initial description satisfies a predetermined correlation criterion, this step is performed from similarity coefficients cited in the preceding paragraph, a step of preparing the hypothetical physico-chemical vector from the list of possible molecules and from test physico-chemical vectors associated with the test odors and/or aromas included in the color series with which the initial description satisfies the correlation criterion, the hypothetical physico-chemical vector comprising hypothetical proportions associated with the respective possible molecules.

17. The method as claimed in claim 14, in which the following steps are implemented by a computer: the second step of assigning a colorimetric description, the first learning step, the error computation step, the step of updating the physico-chemical vector.

* * * * *